(12) United States Patent
Minami et al.

(10) Patent No.: US 9,539,280 B2
(45) Date of Patent: Jan. 10, 2017

(54) CARTILAGE PRODUCTION PROMOTER AND PROPHYLACTIC OR THERAPEUTIC AGENT FOR DISEASES ASSOCIATED WITH CARTILAGE DAMAGE

(71) Applicants: NATIONAL UNIVERSITY CORPORATION TOTTORI UNIVERSITY, Tottori (JP); MARINE PRODUCTS KIMURAYA CO., LTD., Tottori (JP)

(72) Inventors: Saburo Minami, Tottori (JP); Yoshiharu Okamoto, Tottori (JP); Yasunari Miki, Tottori (JP)

(73) Assignees: NATIONAL UNIVERSITY CORPORATION TOTTORI UNIVERSITY, Tottori (JP); MARINE PRODUCTS KIMURAYA CO., LTD., Tottori (JP)

( * ) Notice: Subject to any disclaimer, the term of this patent is extended or adjusted under 35 U.S.C. 154(b) by 0 days.

(21) Appl. No.: 14/327,928

(22) Filed: Jul. 10, 2014

(65) Prior Publication Data
US 2014/0323432 A1 Oct. 30, 2014

Related U.S. Application Data

(62) Division of application No. 13/258,270, filed as application No. PCT/JP2009/071613 on Dec. 25, 2009, now abandoned.

(30) Foreign Application Priority Data

Mar. 25, 2009 (JP) ................. 2009-073856

(51) Int. Cl.
*A61K 31/737* (2006.01)
*A61K 31/726* (2006.01)
*C08B 37/00* (2006.01)

(52) U.S. Cl.
CPC ........... *A61K 31/737* (2013.01); *A61K 31/726* (2013.01); *C08B 37/0036* (2013.01)

(58) Field of Classification Search
CPC .. A61K 31/726; A61K 31/737; C08B 37/0036
USPC ......................................................... 514/54
See application file for complete search history.

(56) References Cited

U.S. PATENT DOCUMENTS 5,629,009 A * 5/1997 Laurencin et al. ........... 424/426
6,207,652 B1 * 3/2001 Sakai .................. A61K 31/737
514/25
6,812,220 B2 11/2004 Jackson et al.
7,678,368 B2 * 3/2010 Mizutani .................. A61K 8/60
424/401
2003/0064958 A1 4/2003 Jackson et al.
2006/0051316 A1 * 3/2006 Ohnogi et al. ............. 424/78.31

FOREIGN PATENT DOCUMENTS

| EP | 1 226 826 A1 | 7/2002 | |
|---|---|---|---|
| JP | 2000-169322 | 6/2000 | |
| JP | 2004-10533 | 1/2004 | |
| JP | 2005-82806 | 3/2005 | |
| JP | 2005-508893 | 4/2005 | |
| JP | 2006-233099 | 9/2006 | |
| WO | 01/13925 | 3/2001 | |
| WO | 01/82936 | 11/2001 | |
| WO | 01/82936 A1 | 11/2001 | |
| WO | 2004/050078 | 6/2004 | |
| WO | 2006/090815 | 8/2006 | |
| WO | 2006/128100 | 11/2006 | |
| WO | WO 2006/128100 A2 * | 11/2006 | ............. A61K 35/14 |
| WO | 2007/127298 | 11/2007 | |

OTHER PUBLICATIONS

Tanpakusitu kakusan Koso 1995, 40(5), pp. 467-474; English Translation of Abstract.*
The Merck Manual, 1992, pp. 1338-1340.*
Decision of Rejection issued Nov. 11, 2014 in corresponding Japanese Patent Application No. 2011-505815, with partial English translation.
Fuminori Ohtaka et al., "Effects of rhBMP-2 on Metabolism of Proteoglycan in Rabbit Chondrocytes", Kitasato Medicine, vol. 28, pp. 58-64, 1998, with English Abstract.
A. Hari Reddi, Tanpakusitu, Kakusan, Koso, vol. 40, No. 5, pp. 467-474, 1995, with partial English translation of Abstract.
Fujio Suzuki, Tanpakusitu, Kakusan, Koso, vol. 40, No. 5, pp. 506-519, 1995, with partial English translation.
International Search Report issued Feb. 2, 2010 in International (PCT) Application No. PCT/JP2009/071613.
International Preliminary Report on Patentability issued Nov. 3, 2011 in International (PCT) Application No. PCT/JP2009/071613.
Yasunori Tamai et al., "Enhanced healing of cartilaginous injuries by glucosamine hydrochloride", Carbohydrate Polymers, vol. 48, 2002, pp. 369-378.
Yasunori Tamai et al., "Enhanced healing of cartilaginous injuries by N-acetyl-D-glucosamine and glucuronic acid", Carbohydrate Polymers, vol. 54, 2003, pp. 251-262.
The Merck Manual, 1992, pp. 1338-1341.

* cited by examiner

*Primary Examiner* — Ganapathy Krishnan
(74) *Attorney, Agent, or Firm* — Wenderoth, Lind & Ponack, L.L.P.

(57) ABSTRACT

Disclosed is a therapy which is for preventing or treating cartilage damage and diseases associated with cartilage damage, such as arthritides and osteoarthritis, and utilizes a more effective and more safe medicinal agent. Specifically disclosed are a cartilage production promoter, a glucosaminoglycan and/or proteoglycan production promoter, and a prophylactic or therapeutic agent for diseases associated with cartilage damage, each of which comprises fucoidan as an active ingredient.

4 Claims, 13 Drawing Sheets

FIG. 1: Remarks obtained by macroscopic observing the damaged joint sites
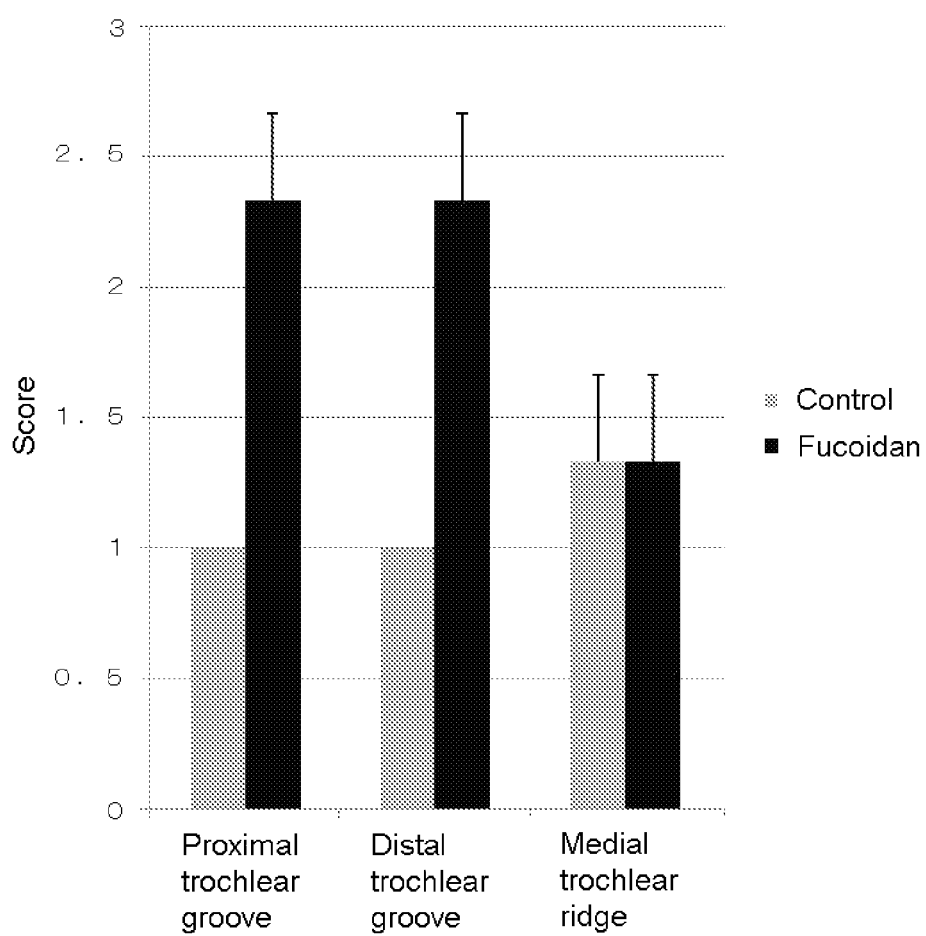

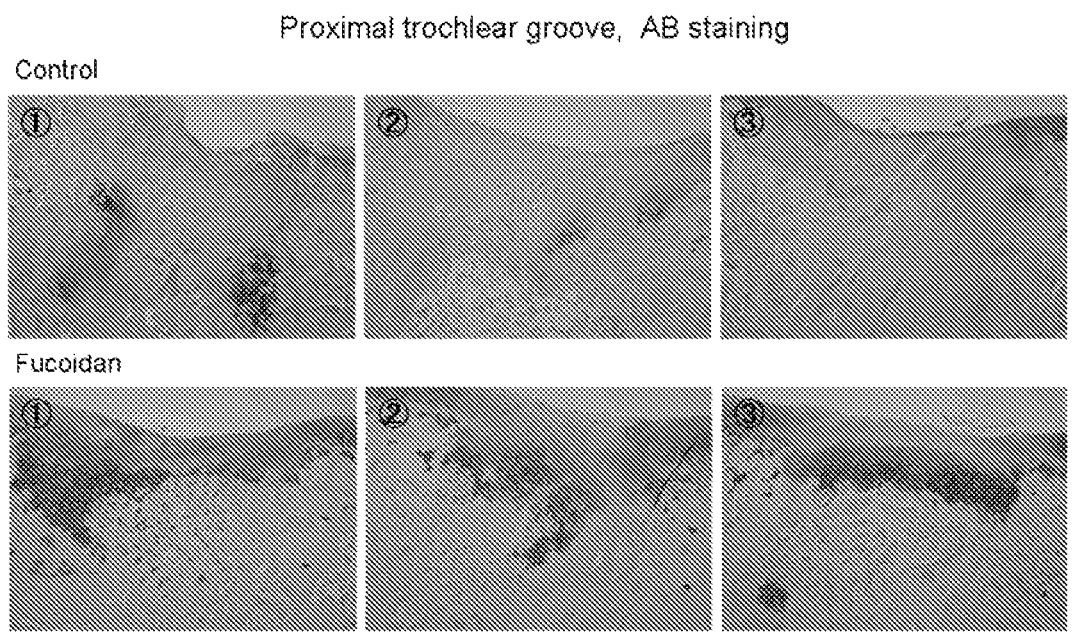
FIG. 2: Histological remark of damaged joint sites (damaged sites of proximal trochlear groove)
Numbers ①, ②, and ③ show rabbit individuals in respective groups.
The upper shows the control group, and the lower shows the fucoidan group.

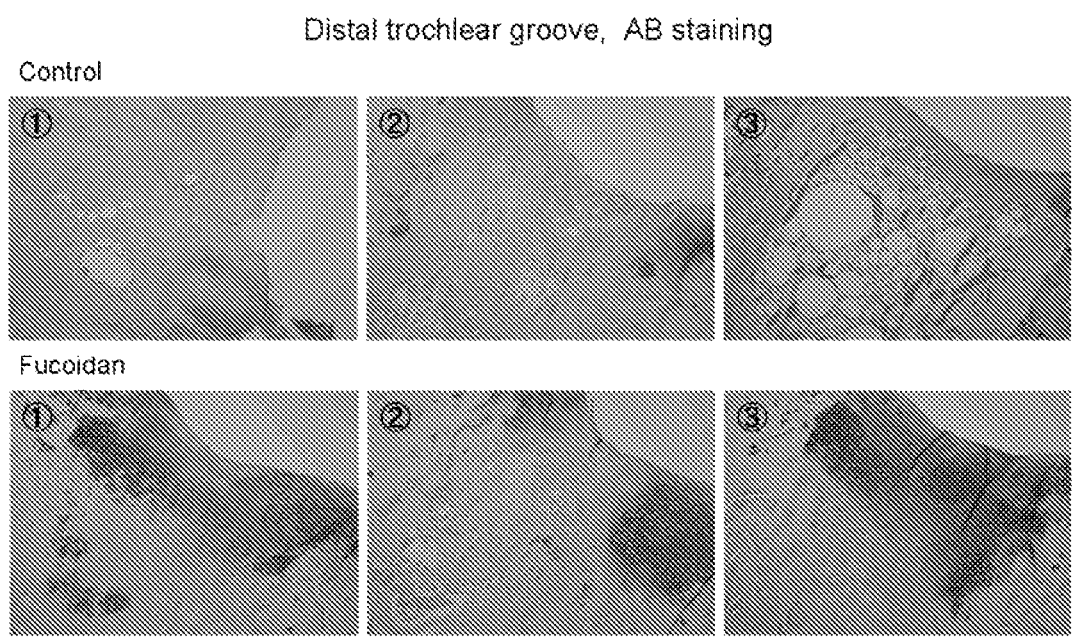
FIG. 3: Histological remark of damaged joint sites (damaged sites of distal trochlear groove)
Numbers ①, ②, and ③ show rabbit individuals in respective groups.
The upper shows the control group, and the lower shows the fucoidan group.

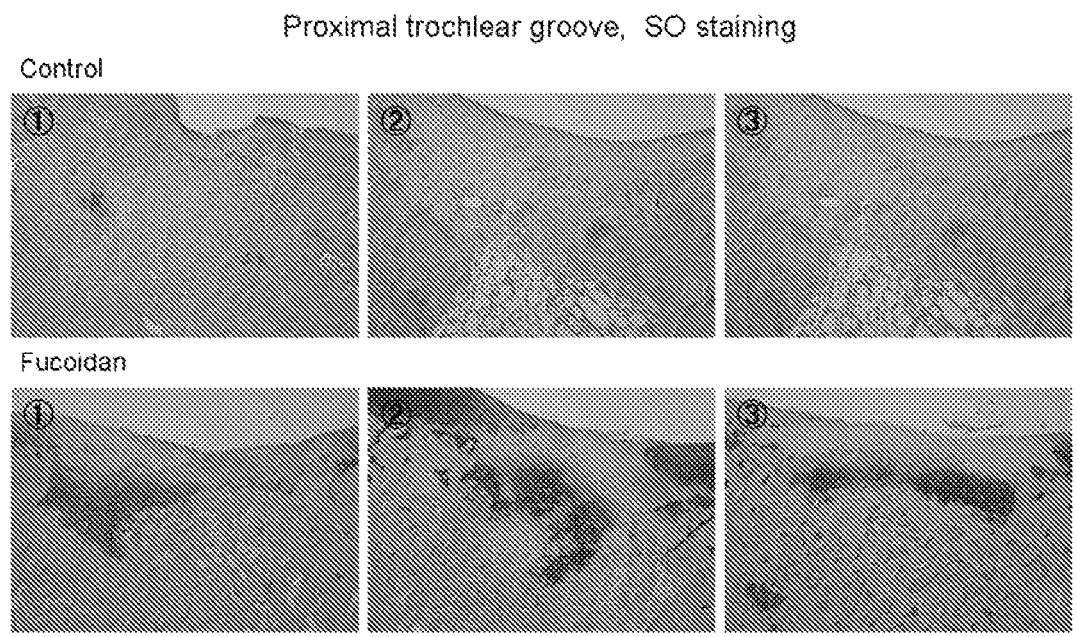
FIG. 4: Histological remark of damaged joint sites (damaged sites of proximal trochlear groove)
Numbers ①, ②, and ③ show rabbit individuals in respective groups.
The upper shows the control group, and the lower shows the fucoidan group.

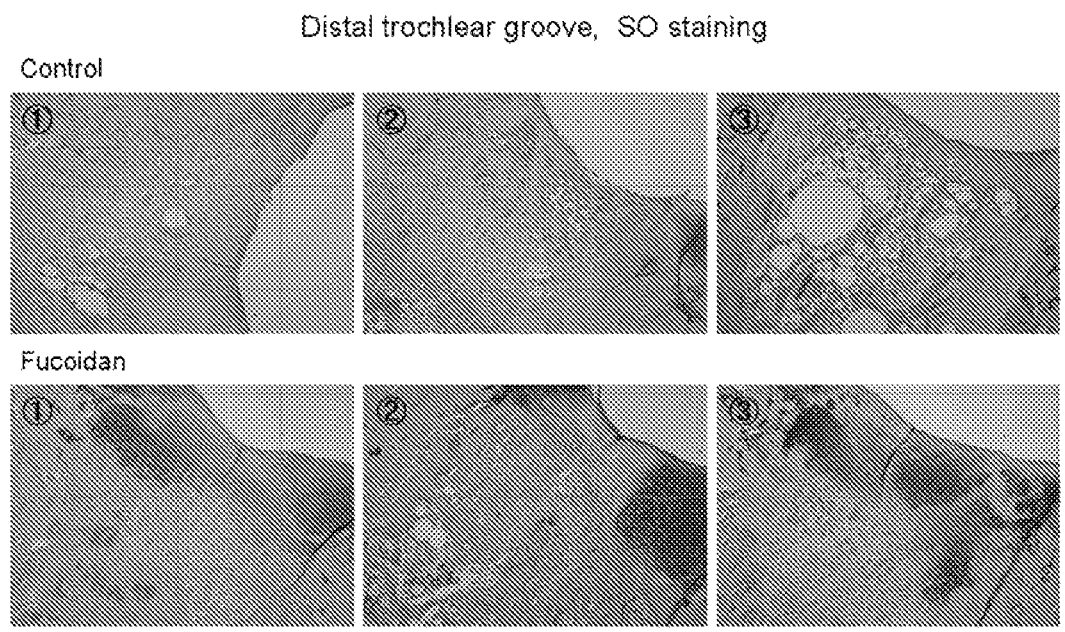
FIG. 5: Histological remark of damaged joint sites (damaged sites of distal trochlear groove)
Numbers ①, ②, and ③ show rabbit individuals in respective groups.
The upper shows the control group, and the lower shows the fucoidan group.

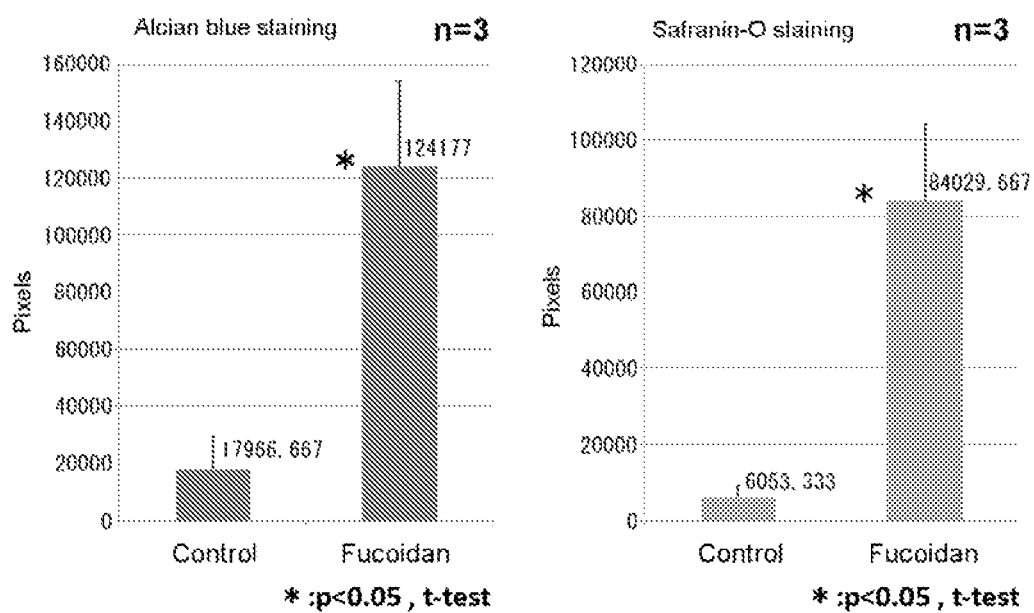
FIG. 6: Image analysis results of damaged sites

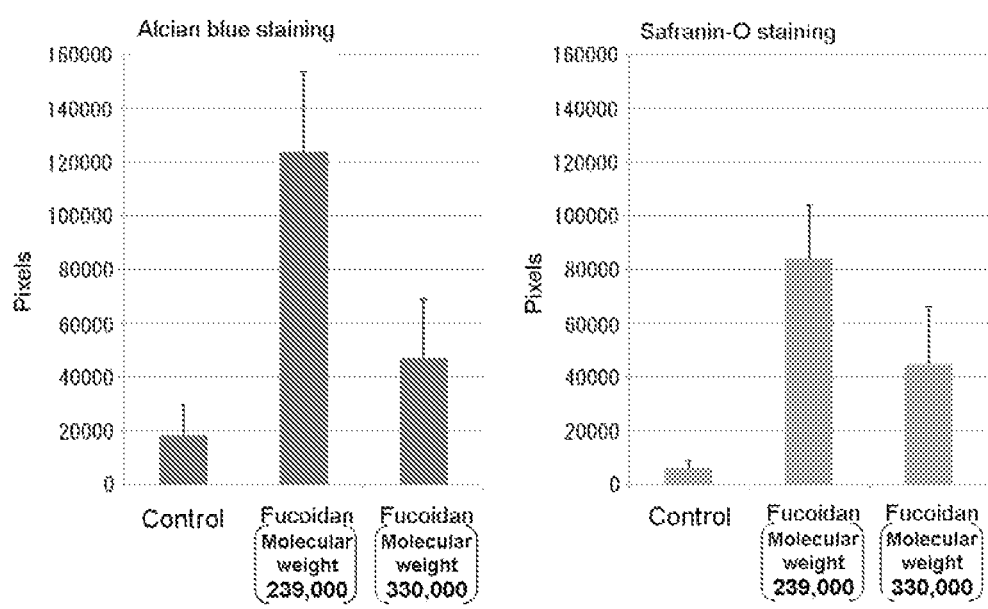
FIG. 7: Difference in repair degree dependent on fucoidan molecular weight
Fucoidan: Cartilage-repairing effect dependent on molecular weight

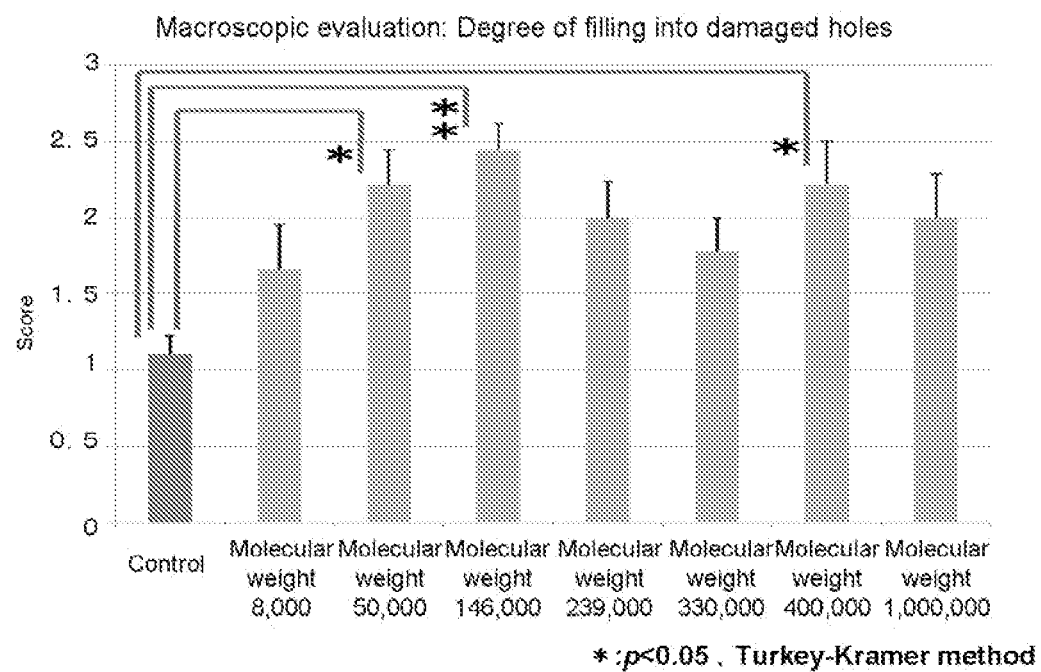
FIG. 8: Difference in repair degree dependent on fucoidan molecular weight (macroscopic observation)

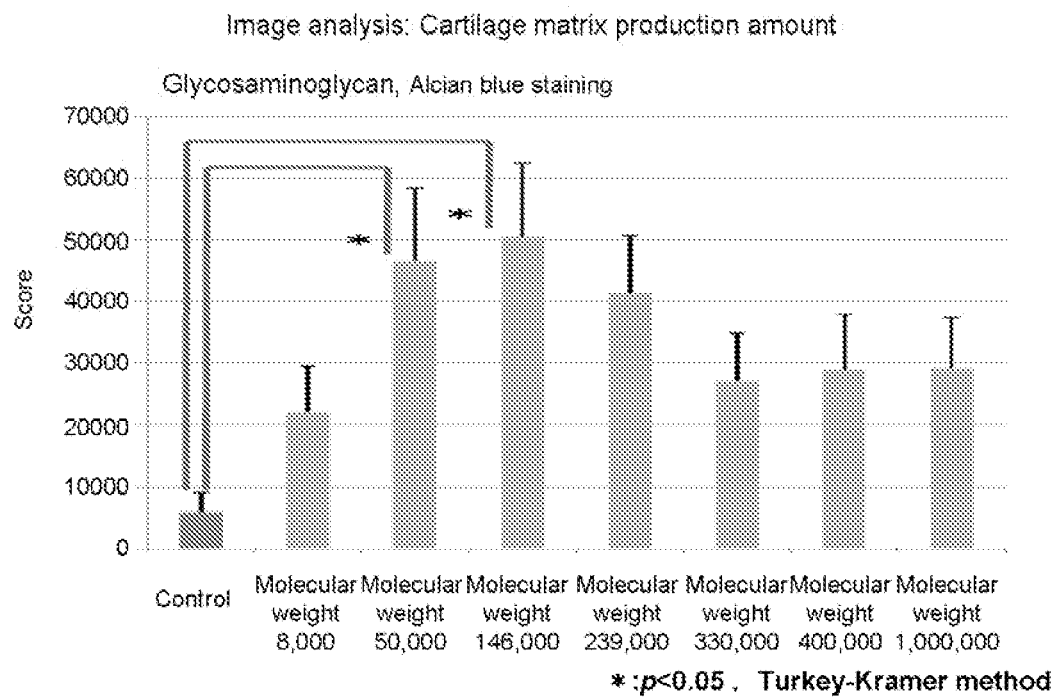
FIG. 9: Difference in repair degree dependent on fucoidan molecular weight (through image analysis results of damaged sites)

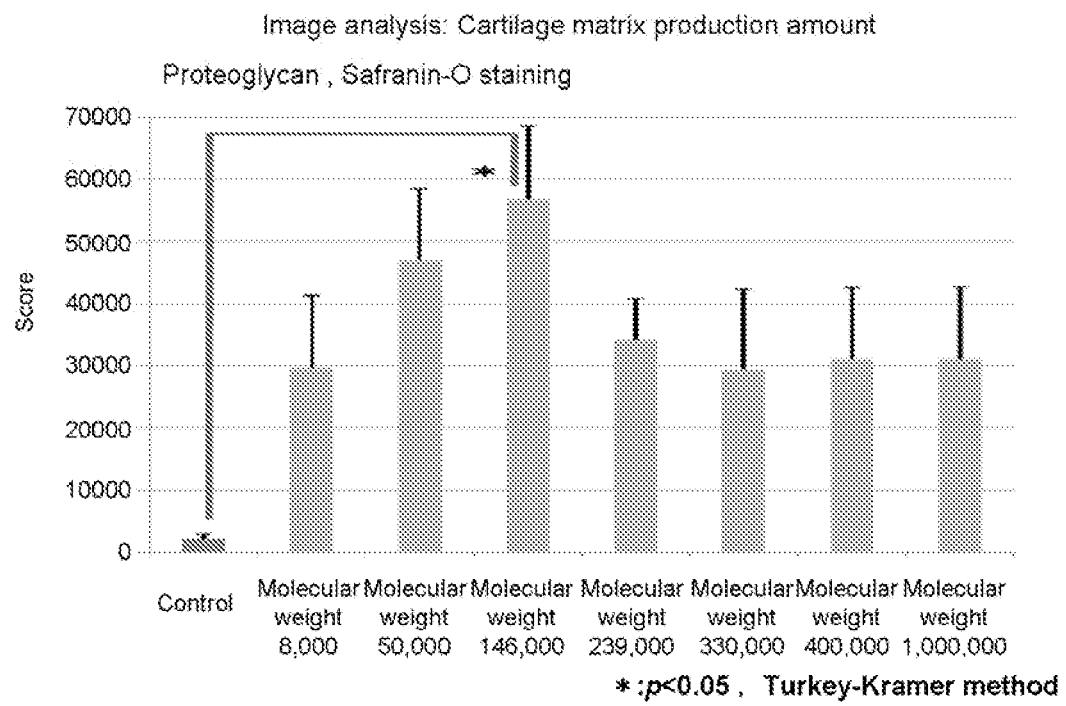
FIG. 10: Difference in repair degree dependent on fucoidan molecular weight (through image analysis results of damaged sites)

FIG. 11: Histological remark of damaged sites
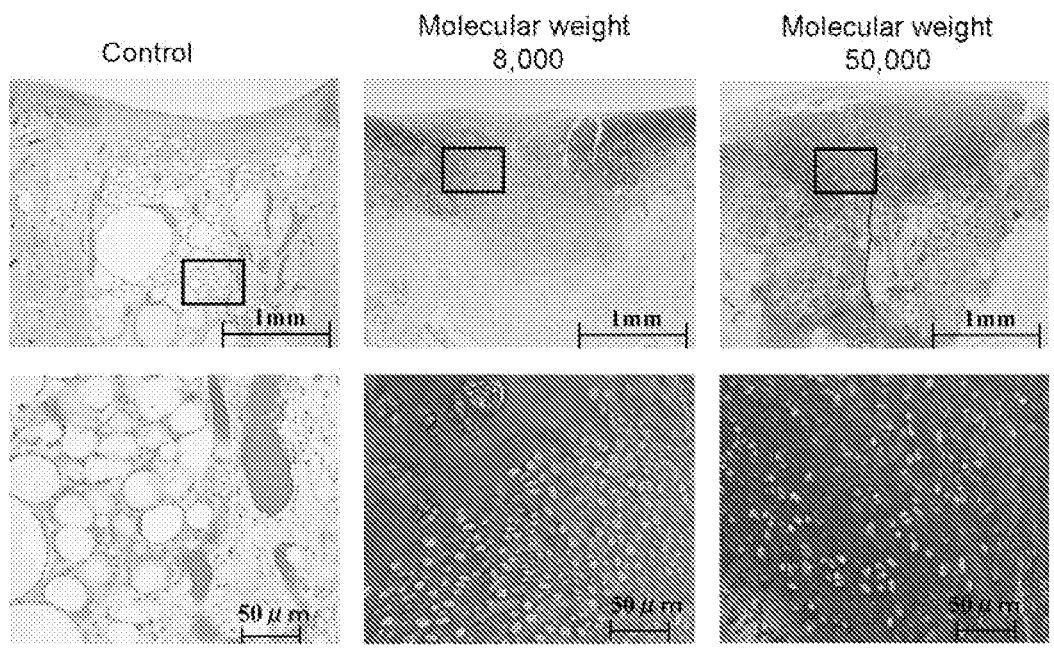
Lower image shows enlarged image of rectangular region in the corresponding upper image.

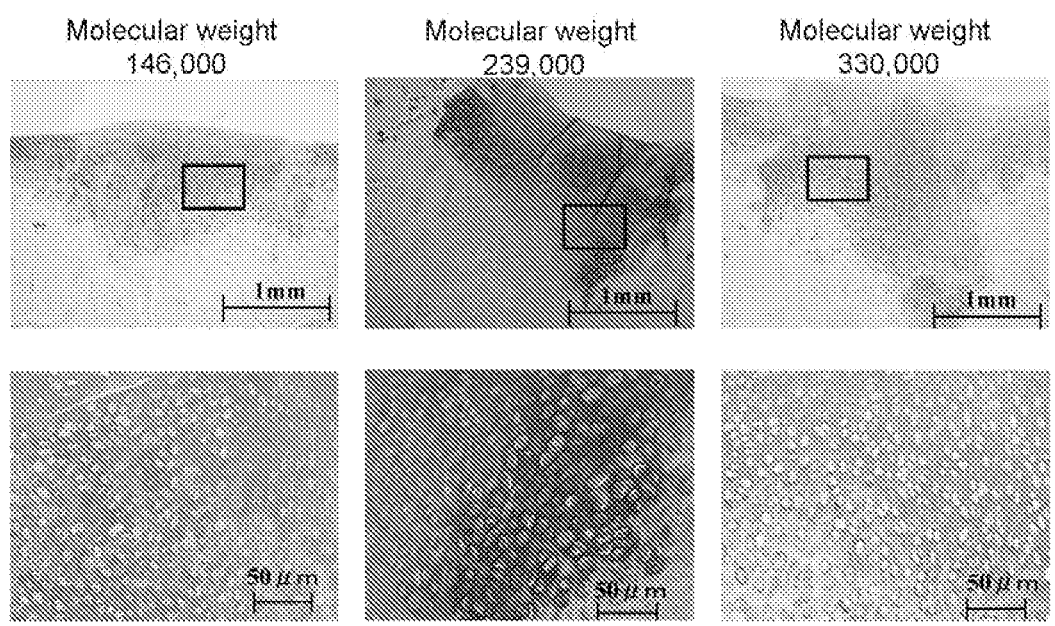
FIG. 12: Histological remark of damaged sites
Lower image shows enlarged image of rectangular region in the corresponding upper image.

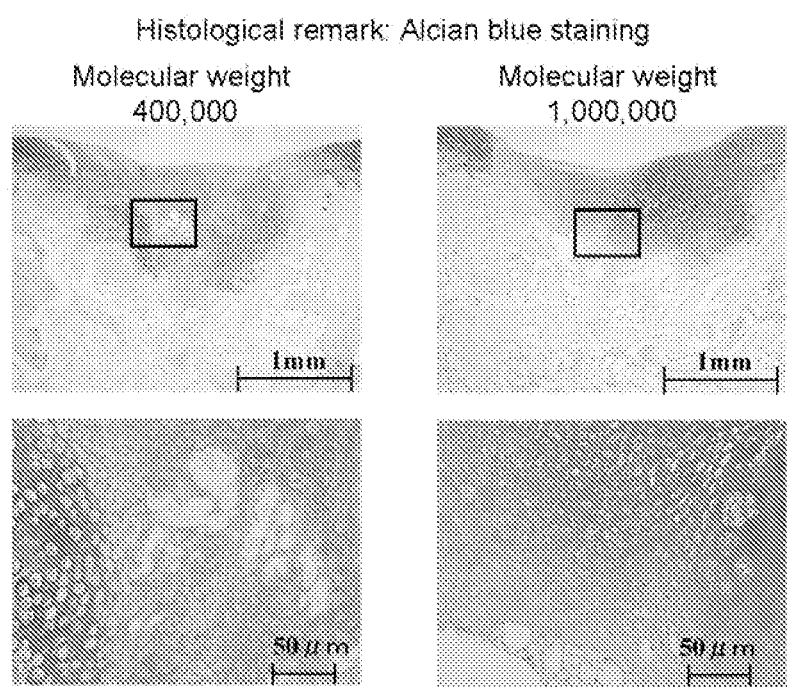
FIG. 13: Histological remark of damaged sites
Lower image shows enlarged image of rectangular region in the corresponding upper image.

CARTILAGE PRODUCTION PROMOTER AND PROPHYLACTIC OR THERAPEUTIC AGENT FOR DISEASES ASSOCIATED WITH CARTILAGE DAMAGE

RELATED APPLICATION

This application claims the benefit of the priority of Japanese Patent Application No. 2009-73856 filed to the Japanese Patent Office on Mar. 25, 2009. The patent application to which this application claims priority is incorporated into the present specification by reference in its entirety.

TECHNICAL FIELD

The present invention relates to a chondrogenesis promoter, a glycosaminoglycan and/or proteoglycan production promoter, and a prophylactic or therapeutic agent for a cartilage damage and a disease due to a cartilage damage, which contain a fucoidan as an effective component.

BACKGROUND ART

Cartilage is a tissue composed of a cartilage matrix and cartilage cells (chondrocytes) spotted therein. The cartilage matrix is composed of water, collagen, proteoglycan, and others. Proteoglycan is a complex composed of a polysaccharide called glycosaminoglycan, and a protein. Cartilage fulfills various functions in the living body through the elasticity thereof.

Diseases due to a cartilage damage include various diseases such as arthrosis deformans, arthritis and rheumatism. As therapeutic agents for these diseases, many effective components such as glucosamine (see Non-Patent Document 1) and glucuronic acid (Patent Document 1) are known.

Fucoidan is a polysaccharide contained in marine alga (for example, mozuku (*Nemacystus decipiens*), Japanese kelp (*Laminaria japonica*) etc.), and has been ingested from early times by eating of these marine alga. Fucoidan has many physiological activity functions such as immunostimulatory activity, adhesion-preventing activity and anti-inflammatory activity (see Patent Documents 2 and 3, and others).

Patent Document 4 describes that fucoidan promotes a morphogenetic action of bone and cartilage. However, the disclosure of Patent Document 4 is merely about an agent for promotion of osteogenesis. Osteoblast is necessary to induce bone, and chondroblast is necessary to induce cartilage. Osteoblast and chondroblast are each derived by differentiation or induction from undifferentiated cells in accordance with different systems. Osteoblast and chondroblast are entirely different cells, and are also different from each other in their properties and functions. Osteoblast produces type I collagen, and calcifies it with alkaline phosphatase activity, so as to ossify. Chondroblast, which is cartilage cell precursor, produces type II collagen or glycosaminoglycan and is differentiation-induced to cartilage cell. The cartilage cell synthesizes proteoglycan around the cells, thereby blocking calcification and bone formation based on osteoblast to form cartilage. For the formation of cartilage, ossification is required to be inhibited. The cartilage formation is a promoting of synthesis of proteoglycan by cartilage cell. Thus the cartilage formation is a biological phenomenon which is entirely different from the bone formation. In other words, Patent Document 4 discloses a reverse effect to a matter that fucoidan promotes the formation of cartilage.

In Examples of Patent Document 4, results obtained by administering fucoidan or the like directly into established cell lines are disclosed. However, according to any ordinary administering manner such as oral ingestion, fucoidan is never directly contacted with osteoblast. In conclusion, Patent Document 4 never discloses what effect is produced when fucoidan is administered into an actual living body.

As described above, there has not been any finding that fucoidan itself has an effect of promoting a chondrogenesis.

Patent Document 1: JP-A-2004-10533
Patent Document 2: JP-A-2005-82806
Patent Document 3: JP-A-2005-508893
Patent Document 4: JP-A-2004-10533
Non-Patent Document 1: Tamai et al., Carbohydrate Polymers, 2002, vol. 48, pp. 369-378

DISCLOSURE OF THE INVENTION

Problems to be Solved by the Invention

Many patients suffer from arthropathy, and further it is anticipated that patients of senile arthrosis will increase hereafter as the population ages in Japan. In such a situation, there are still desires for more useful therapeutic agents capable of repairing a cartilage damage. It should be preferred that such therapeutic agents are safe and free from any side effects, and can prevent diseases when routinely ingested.

Means for Solving the Problems

The present inventors have intensively studied to solve the problems, and a result, have found out fucoidan as a substance for solving the problems. Thus, the present invention has been completed.

That is, the present invention provides:

(1) A chondrogenesis promoter comprising a fucoidan as an effective component, (2) The chondrogenesis promoter according to (1), wherein the fucoidan has a molecular weight of 8,000 to 400,000, (3) The chondrogenesis promoter according to (1), wherein the fucoidan has a molecular weight of 50,000 to 150,000, (4) A glycosaminoglycan and/or proteoglycan production promoter comprising a fucoidan as an effective component, (5) The glycosaminoglycan and/or proteoglycan production promoter according to (2), wherein the fucoidan has a molecular weight of 8,000 to 400,000, (6) The glycosaminoglycan and/or proteoglycan production promoter according to (2), wherein the fucoidan has a molecular weight of 50,000 to 150,000, (7) A pharmaceutical or veterinary medical agent composition for preventing or treating a cartilage damage and a disease due to a cartilage damage, comprising a fucoidan as an effective component, (8) The pharmaceutical or veterinary medical agent composition according to (7), wherein the fucoidan has a molecular weight of 8,000 to 400,000, (9) The pharmaceutical or veterinary medical agent composition according to (7), wherein the fucoidan has a molecular weight of 50,000 to 150,000,

(10) Use of a fucoidan in a production of a pharmaceutical or veterinary medical agent composition for preventing or treating a cartilage damage and a disease due to a cartilage damage,

(11) The use according to (10), wherein the fucoidan has a molecular weight of 8,000 to 400,000,

(12) The use according to (10), wherein the fucoidan has a molecular weight of 50,000 to 150,000,

(13) A method for preventing or treating a cartilage damage or a disease due to a cartilage damage, which comprises administering a fucoidan in an effective amount to an animal,

(14) The method according to (13), wherein the fucoidan has a molecular weight of 8,000 to 400,000, and

(15) The method according to (13), wherein the fucoidan has a molecular weight of 50,000 to 150,000.

Effects of the Invention

According to the present invention, a chondrogenesis promoter, a glycosaminoglycan and/or proteoglycan production promoter, and a prophylactic or therapeutic agent for a cartilage damage and a disease due to a cartilage damage, which contain a fucoidan as an effective component, are obtained. These are useful for preventing and treating, for example, arthrosis deformans, senile arthrosis, and articular rheumatism. Since these contain a fucoidan, which is a natural substance contained in marine algae, these are high in safety and give no side-effect.

BRIEF DESCRIPTION OF THE DRAWINGS

FIG. 1 shows visual evaluation and comparison of the extent of healing of damages in the control group and the fucoidan-administered group.

FIG. 2 shows results obtained by staining proximal trochlear grooves of the control group and those of the fucoidan-administered group with alcian blue. The numbers 1, 2 and 3 show the rabbit individuals in the respective groups; and the upper shows the control group, and the lower shows the fucoidan-administered group.

FIG. 3 shows results obtained by staining distal trochlear grooves of the control group and those of the fucoidan-administered group with alcian blue. The numbers 1, 2 and 3 show the rabbit individuals in the respective groups; and the upper shows the control group, and the lower shows the fucoidan-administered group.

FIG. 4 shows results obtained by staining proximal trochlear grooves of the control group and those of the fucoidan-administered group with safranin-O. The numbers 1, 2 and 3 show the rabbit individuals in the respective groups; and the upper shows the control group, and the lower shows the fucoidan-administered group.

FIG. 5 shows results obtained by staining distal trochlear grooves of the control group and those of the fucoidan-administered group with safranin-O. The numbers 1, 2 and 3 show the rabbit individuals in the respective groups; and the upper shows the control group, and the lower shows the fucoidan-administered group.

FIG. 6 shows results obtained by analyzing alcian blue-stained images and safranin-O-stained images of damaged site samples.

FIG. 7 shows results obtained by analyzing alcian blue-stained images and safranine-O-stained images about a control group, and damaged site samples in which fucoidans having a molecular weight of 239,000, and 330,000 were each administered.

FIG. 8 shows visual evaluation and comparison of the extent of healing of damages in a control group, and fucoidan-administered groups in which fucoidans having different molecular weights were each administered.

FIG. 9 shows results obtained by analyzing alcian blue-stained images of damaged site samples of a control group, and fucoidan-administered groups in which fucoidans having different molecular weight were each administered.

FIG. 10 shows results obtained by analyzing safranine-O-stained images of damaged site samples of a control group, and fucoidan-administered groups in which fucoidans having different molecular weight were each administered.

FIG. 11 shows results obtained by staining damaged sites of a control group and groups of 8,000 and 50,000 in molecular weight with alcian blue. Each image in the lower in the view shows an enlarged image of a rectangular region in the corresponding image in the upper.

FIG. 12 shows results obtained by staining damaged sites of groups of 146,000, 239,000, and 330,000 in molecular weight with alcian blue. Each image in the lower in the view shows an enlarged image of a rectangular region in the corresponding image in the upper.

FIG. 13 shows results obtained by staining damaged sites of groups of 400,000, and 1,000,000 in molecular weight with alcian blue. Each image in the lower in the view shows an enlarged image of a rectangular region in the corresponding image in the upper.

BEST MODE FOR CARRYING OUT THE INVENTION

The present inventors have found out that fucoidan has a function of promoting a chondrogenesis, and repairing a damage of cartilage. The present inventors have further found out that fucoidan promotes the production of glycosaminoglycan and proteoglycan. Fucoidan is a polysaccharide contained in marine algae (for example, mozuku (*Nemacystus decipiens*) and Japanese kelp (*Laminaria japonica*) etc.), and has been ingested from early times by the eating of these marine alga. Fucoidan has many physiological activity functions such as immunostimulatory activity, adhesion-preventing activity, and anti-inflammatory activity. However, there has not been any finding that fucoidan itself has an effect of promoting the chondrogenesis.

In the first aspect, the present invention provides a chondrogenesis promoter containing a fucoidan as an effective component.

In the second aspect, the present invention provides a glycosaminoglycan and/or proteoglycan production promoter containing a fucoidan as an effective component.

In the third aspect, the present invention provides a prophylactic or therapeutic agent for a cartilage damage and a disease due to a cartilage damage, containing a fucoidan as an effective component.

The chondrogenesis promoter, the glycosaminoglycan and/or proteoglycan production promoter and the prophylactic or therapeutic agent for a cartilage damage and a disease due to a cartilage damage, of the present invention, are useful for preventing or treating symptoms related to a cartilage damage, for example, arthrosis deformans, senile arthrosis, articular rheumatism, spondylitis deformans, articular sprain, and ligament damage.

The fucoidan used as an effective component in the chondrogenesis promoter, the glycosaminoglycan and/or proteoglycan production promoter and the prophylactic or therapeutic agent thereof for a cartilage damage and a disease due to a cartilage damage, of the present invention, can be a purified product, or a roughly purified product, for example, an extract from marine algae such as mozuku. The method or means for extracting fucoidan from fucoidan-containing materials such as marine algae is well known. The fucoidan used in the present invention can be in the form of a solid (such as powder and granule), a liquid (such as aqueous solution of fucoidan, fucoidan suspension and extract from marine algae), or a semi-solid (such as paste). In the present invention, a fucoidan-containing material can be contained as an effective component. Preferred examples of the fucoidan-containing material include marine algae, in particular brown algae. Examples of fucoidan-containing brown algae include mozuku (for example, okinawamozuku (*Cladosiphon okamuranus*) and itomozuku (*Nemacystus decipiens*)), wakame (*Undaria pinnatifida*), mekabu (sporophyl of wakame), arame (*Eisenia bicyclis*), gagome (*Kjellmaniella crassifolia*), Japanese kelp (*Laminaria japonica*), kurome (*Eckronia kurome*), kajime (*Kjellmaniella crassifalia*), mitsuishikonbu (*Laminaria angustata*), yoremoku (*Sargassum siliquastrum*), hiziki (*Hizikia fusiformis*), hondawara (*Sargassum fulvellum*), yatsumatamoku (*Sargassum patens*), akamoku (*Sargassum horneri*), Arctic wrack (*Focus evanescens*), and umitoranoo (*Sargassum thunbergii*). However, the invention is not limited by the examples.

The chondrogenesis promoter, the glycosaminoglycan and/or proteoglycan production promoter, and the prophylactic or therapeutic agent for a cartilage damage and a disease due to a cartilage damage, of the present invention, can be in the form of a pharmaceutical composition. The method for administering the composition is not particularly limited, and can be any method such as an oral, injection, or percutaneous method. An oral administration is preferred. In the case of an oral administration agent, the composition can be formulated into various oral agent forms such as condensate, powder, granule, tablet, capsule agent and drinking agent. Methods for producing these agent forms are well known, and the following processes can be appropriately used: mixing, dissolving, pulverizing, tableting, drying, and others. A carrier, or excipient can be used in accordance with the purpose of the pharmaceutical composition. A flavor, a sweetener, a colorant and/or some other can be appropriately added to any oral administration agent of the present invention. The oral administration agent of the present invention can be administered as it is, or can be administered in the state that the agent is appropriately added to a food or drink such as miso soup and tea since the fucoidan as an effective component has no taste and smell.

The chondrogenesis promoter, the glycosaminoglycan and/or proteoglycan production promoter, and the prophylactic or therapeutic agent for a cartilage damage and a disease due to a cartilage damage, of the present invention, can be in the form of a food or drink. Since fucoidan itself has no taste and smell, fucoidan is used to produce various foods or drinks without producing any effect onto flavor and taste. For example, miso soup or soup can be produced into which fucoidan powder, or an fucoidan extract from mozuku or some other is incorporated. Alternatively, the promoter or agent of the present invention can be made into a form obtained by concentrating a fucoidan extract from mozuku or some other and packaging the concentrate into a package, or subjecting the extract to freeze-drying or some other treatment to make the concentrate into a powder or granular form or some other form and then putting the resultant into an appropriate packaging or container, or by subjecting the extract to some other processing, and thereby, users themselves can add the promoter or agent of the present invention to any foods or drinks to ingest.

The chondrogenesis promoter, the glycosaminoglycan and/or proteoglycan production promoter, and the prophylactic or therapeutic agent for a cartilage damage and a disease due to a cartilage damage, of the present invention, can be a supplement containing a fucoidan or a fucoidan-containing material. The supplement can be made into the form of tablet, capsule agent, granule, powder, or some other by a method well known by those skilled in the art. As described herein, when the food or drink according to the present invention is used, a user or a patient can ingest the fucoidan routinely over a long term without hesitation. Thus, the promoter or agent of the present invention can contribute to the prevention and the treatment of the above-mentioned diseases. The food or drink according to the present invention is useful also as a functional food.

A dose of the chondrogenesis promoter, the glycosaminoglycan and/or proteoglycan production promoter, and the prophylactic or therapeutic agent for a cartilage damage and a disease due to a cartilage damage, of the present invention, can be decided by those skilled in the art without difficulty. For example, the amount of the fucoidan to be administrated can be decided while the preventing or treating effect against a target disease such as arthrosis deformans, senile arthrosis and articular rheumatism is observed. The amount (dry amount) of the fucoidan to be administered through the agent of the present invention is usually from about 0.3 g or more per day, preferably about 1 g or more per day for an adult.

The chondrogenesis promoter, the glycosaminoglycan and/or proteoglycan production promoter, and the prophylactic or therapeutic agent for a cartilage damage and a disease due to a cartilage damage, of the present invention, can contain one or more effective components other than fucoidan. Examples of the other effective component include known anti-inflammatory agents, and other therapeutic agents (for example, glucosamine etc.) for diseases due to a cartilage damage.

Furthermore, the present invention provides the use of a fucoidan in the production of a chondrogenesis promoter, a glycosaminoglycan and/or proteoglycan production promoter, and a prophylactic or therapeutic agent for a cartilage damage and a disease due to a cartilage damage.

In another aspect, the present invention provides a veterinary medical agent, for preventing or treating a cartilage damage and a disease due to a cartilage damage, that contains a fucoidan as an effective component. The veterinary medical agent can be in the form of a veterinary medical agent composition. The method for administrating the veterinary medical agent is not particularly limited, and can be any method such as oral, injection and percutaneous method. Oral administration is preferred. In the case of an oral administration agent, the composition can be formulated into various oral agent forms, such as condensate, powder, granule, tablet, capsule agent and drinking agent. Methods for producing these agent forms are well known, and the following processes can be appropriately used: mixing, dissolving, pulverizing, tableting, drying, and others. A carrier, or excipient acceptable for veterinary medical agents can be used. A flavor, a sweetener, a colorant and/or some other can be appropriately added to any oral administration agent of the present invention. The veterinary medical agent can contain one or more other effective components other than fucoidan. Examples of the other effective component include known anti-inflammatory agents and therapeutic agents (for example, glucosamine etc.) for diseases due to a cartilage damage.

The present invention further provides the use of a fucoidan in the production of a veterinary medical agent for preventing or treating a cartilage damage and a disease due to a cartilage damage.

The present invention further provides a method for preventing or treating a cartilage damage and a disease due to a cartilage damage in a target animal which includes a human or does not include human, in which a fucoidan is administered in an effective amount to the animal.

The molecular weight of the fucoidan as an effective component in the present invention is preferably in the range of 8,000 to 1,000,000, for example, 8,000 to 250,000, 250,000 to 500,000, 500,000 to 750,000, 750,000 to 1,000,000, 8,000 to 350,000, 350,000 to 1,000,000, 50,000 to 1,000,000, 150,000 to 1,000,000, 250,000 to 1,000,000, 400,000 to 1,000,000 or the like. The molecular weight is more preferably in the range of 8,000 to 40,000, for example, 8,000 to 150,000, 150,000 to 250,000, 250,000 to 350,000, 350,000 to 400,000, 50,000 to 350,000, 50,000 to 400,000, 150,000 to 350,000, 150,000 to 400,000, 250,000 to 400,000 or the like. The molecular weight is even more preferably in the range of 8,000 to 250,000, for example, 8,000 to 50,000, 50,000 to 100,000, 100,000 to 200,000, 8,000 to 150,000, 150,000 to 250,000, 50,000 to 250,000 or the like. The molecular weight is further preferably in the range of 50,000 to 150,000, for example, 50,000 to 100,000, 100,000 to 150,000 or the like. The molecular weight of 150,000 is most preferably.

The molecular weight of the fucoidan can be measured by a well known method, for example, gel filtration chromatography. Usually, pullulan having an already known molecular weight is used as a marker when the molecular weight is measured. Generally, the molecular weight of polymeric compound is represented by the average molecular weight, the number-average molecular weight or the weight-average molecular weight. In the specification, the term "molecular weight" denotes weight-average molecular weight unless otherwise specified. The weight-average molecular weight can be calculated by a well known means or method, and for example, can be calculated from the pattern of gel filtration chromatography.

When any molecular weight is represented by a numerical value in the specification, the molecular weight include values in the range of about ±20% of the numerical value. For example, in the case of a molecular weight of 50,000, this molecular weight includes molecular weight values of about 40,000 to about 60,000.

Hereinafter, the present invention will be specifically described in more detail by way of examples. However, the present invention is not limited by the examples.

EXAMPLE 1

Example 1

Production of Damaged Models

As animal specimens, groups of female white rabbits (weight: about 2.0 kg) were used, the number of the rabbits in each of the groups being 3. The rabbits were habituated to the environment for one week from the time of delivery. Thereafter, 0.1 mg/kg of medetomidine was subcutaneously injected into each of the rabbits, and 25 mg/kg of Ketalar was intramuscularly injected thereto. About each of the rabbit specimens subjected to the injection anesthesia, the left knee joint was shaved, and then disinfected. Thereafter, approaching from the outside of the knee joint, the articular capsule was opened and the knee joint was exposed completely by shifting the patella to the inside. With reference to the experiment of Tamai et al. (Carbohydrate Polymers, 2002, vol. 48, pp. 369-378), three holes of 2 mm in diameter and 4 mm in depth were bored with a hand-drill at the proximal trochlear groove, distal trochlear groove, and the medial trochlear ridge. Thereafter, the sites were sufficiently rinsed, and then the articular capsule was sutured with 3-0PDS (polydioxanone). The subcutaneous tissue and the skin were simultaneously sutured with stainless steel wires. After the operation, 0.5 mg/kg of atipamezole was diluted and subcutaneously injected two times per day to wake the rabbits.

From the day of the operation, initially every day, water (50 mL) in which 1 g of a fucoidan was dissolved were dosed to the rabbits in the fucoidan-administered group by natural intake. Thereafter, water was given to the rabbits to drink freely. This was continued for 3 weeks. Only water was given to the rabbits in the control group. During this period, there were no signs of side effects or the like in the fucoidan-administered group.

After the end of the fucoidan-administering term of the three weeks, the rabbit specimens in each of the fucoidan-administered group and the control group were euthanized, and then the operated site was exposed.

EXAMPLE 2

Example 2

Macroscopic Observation of the Degree of Healing

The operated site of the left femur in each of the damaged models in Example 1 was macroscopically observed. About the degree of healing after the 3 weeks, many of the damages were satisfactorily cured in the fucoidan-administered group. In the control group, many of the damages were not cured. The degree of healing of each of the damages was scored on the basis of Table 1, and evaluated.

TABLE 1

| Remark through macroscopic observation | Score |
| --- | --- |
| Healing rate of less than 50% | 0 |
| Healing rate of 50% or more and less than 60% | 1 |
| Healing rate of 60% or more and less than 80% | 2 |
| Healing rate of 80% or more | 3 |

The results were as shown in FIG. 1. From the results, in the fucoidan-administered group, good therapeutic results were obtained in the proximal trochlear groove and the distal trochlear groove. In the control group, the damaged sites were filled with collagen fibers, fibroblasts and others. By contrast, in the fucoidan-administered group, the damaged sites were substituted with chondroblasts and cartilage tissues.

EXAMPLE 3

Histological Observation

The left femur of each of the damaged models in Example 1 was recovered, and then fixed with a 10% neutral buffered formalin aqueous solution (formaldehyde solution). The tissue was then decalcified with a 5% formic acid solution under shaking. After the decalcification, the tissue was neutralized with a 5% sodium sulfate solution, and washed with water and then dehydrated. The tissue piece in which the decalcification had been completed was cut so that the repaired sites were positioned on a vertical cross section. Thereafter, the cut tissue was embedded with paraffin in the usual manner, and then sliced with a microtome into thin pieces in thickness of 5 μm. The resultant tissues were used and each stained with alcian blue (AB) and safranin-O (SO) to prepare samples for histological observation. The samples were observed with a microscope, and subjected to image analysis. About the image analysis, a 200-power image of each of the repaired sites was digitized by use of Photograb ab-300 version 1.0 (Macintosh Software, Adobe Systems Inc., Tokyo). Pixels, the number of which was 20,000, were set at random in 6 positions of the image. The number of pixels in which a target color tone occupied was measured. The obtained numerical value was subjected to statistical processing (t-test).

(a) Observed Results of the Staining with Alcian Blue

FIGS. 2 and 3 show results obtained by observing, with the microscope, the proximal and distal trochlear groove in the tissue samples stained with alcian blue. In the fucoidan-administered group, the repaired regions were stained into blue (densely colored regions in the figures). Thus, it showed that a large amount of glycosaminoglycan was contained. By contrast, stained regions were hardly observed in the control group.

(b) Observed Results of the Staining with Safranin-O

FIGS. 4 and 5 show results obtained by observing, with the microscope, the proximal and distal trochlear groove in the tissue samples stained with safranin-O. In the fucoidan-administered group, the repaired regions were stained (densely colored regions in the figures). Thus, it showed that a large amount of proteoglycan was contained. By contrast, stained regions were hardly observed in the control group.

(c) Results of the Image Analysis

FIG. 6 shows results obtained by analyzing the images stained with alcian blue and the images stained with safranin-O by the above-mentioned method. According to the results, the fucoidan-administered group exhibited a significantly higher value about each of the two stains than the control group. Thus, it showed that glycosaminoglycan and proteoglycan were present in a significantly larger amount in the fucoidan-administered group.

According to the results of Examples 2 and 3, it is considered that, in the fucoidan-administered group, the production of glycosaminoglycan and proteoglycan were promoted in the cartilage tissues and that the repair of the cartilage tissues was promoted.

EXAMPLE 4

Example 4

Comparison in the Effects Between Fucoidans Having a Molecular Weight of 239,000 and 330,000

In the production of the same damaged models as in Example 1, fucoidans having a molecular weight of 239,000 and 330,000 were each administered in fucoidan-administered groups. Each of the administered groups were subjected to staining with alcian blue and safranin-O, and image analysis, according to the method of Example 3.

FIG. 7 shows results about the groups in which the fucoidan having the different molecular weights were each administered and the control group. The results were obtained by analyzing the images stained with alcian blue and the images stained with safranin-O by the above-mentioned method. According to the results, in each of the fucoidan-administered groups, the production of glycosaminoglycan and proteoglycan were promoted. In the group in which the smaller-molecular-weight, which was 239,000, fucoidan was administered, glycosaminoglycan and proteoglycan were each produced in a larger amount.

EXAMPLE 5

Example 5

Comparison 1 in the Effects Between Fucoidans Having Molecular Weights Different from Each Other; Production of Damaged Models In the production of the damaged models of Example 1, damaged model groups in which fucoidans having a molecular weight of 8,000, 50,000, 146,000, 239,000, 330,000, 400,000, and 1,000,000 were each administered were produced.

EXAMPLE 6

Example 6

Comparison 2 in the Effects Between Fucoidans Having Molecular Weights Different from Each Other; Macroscopic Observation of the Degree of Healing The operated sites of the left femurs in each of the damaged model groups in Example 5 were macroscopically observed. About each of the damaged model groups, the degree of healing was evaluated on the basis of the criterion in Example 2. The obtained numerical values were subjected to a multiple comparison test according to Turkey-Kramer method. The results were as shown in FIG. 8. From the results, all of the fucoidan-administered groups were better in therapeutic results than the control group. In particular, the groups of 50,000, 146,000, and 400,000 in molecular weight showed better results.

EXAMPLE 7

Example 7

Comparison 3 in the Effects Between Fucoidans Having Molecular Weights Different from Each Other; Histological Observation Each of the damaged model groups in Example 5 was histologically observed according to the method in Example 3. The obtained numerical values were subjected to a multiple comparison test according to Turkey-Kramer method. The results of the image analysis are shown in FIGS. 9 and 10. From the results, all of the fucoidan-administered groups were better in therapeutic results than the control group. In particular, the groups of 50,000, 146,000, and 239,000 in molecular weight showed better results. The group of 146,000 in molecular weight showed the best results.

FIGS. 11 to 13 show microscopically observed results of the alcian blue-stained samples of the control group, and each of the damaged model groups. White dots observed in the fucoidan-administered groups represent chondroblasts. As shown by enlarged images in the lower, it was observed that chondroblasts were activated in each of the damaged models. In the group 146,000 in molecular weight, which showed the best results, it was observed that chondroblasts were further activated.

INDUSTRIAL APPLICABILITY

The present invention is directed to a chondrogenesis promoter, a glycosaminoglycan and/or proteoglycan production promoter, and a prophylactic or therapeutic agent for a cartilage damage and a disease due to a cartilage damage, which contain a fucoidan as an effective component. The present invention provides, for example, a pharmaceutical composition or a food or drink. Thus, the present invention is usable in the field of pharmaceuticals, foods and drinks, and others.

The invention claimed is:

1. A method for promoting chondrogenesis in a human or animal that has arthritis, comprising orally administering an effective amount of a fucoidan having a molecular weight of 146,000 to the human or animal that has arthritis.

2. A method for promoting glycosaminoglycan and/or proteoglycan production in a human or animal that has arthritis, comprising orally administering an effective amount of a fucoidan having a molecular weight of 146,000 to the subject human or animal that has arthritis.

3. The method according to claim 1, wherein the fucoidan is derived from mozuku (Nemacystus decipiens).

4. The method according to claim 2, wherein the fucoidan is derived from mozuku (Nemacystus decipiens).

* * * * *